(12) United States Patent
Rapin et al.

(10) Patent No.: US 10,758,139 B2
(45) Date of Patent: Sep. 1, 2020

(54) AUTOMATIC METHOD TO DELINEATE OR CATEGORIZE AN ELECTROCARDIOGRAM

(71) Applicant: Cardiologs Technologies SAS, Paris (FR)

(72) Inventors: Jeremy Rapin, Paris (FR); Jia Li, Massey (FR); Mathurin Massias, Paris (FR)

(73) Assignee: Cardiologs Technologies SAS, Paris (FR)

( * ) Notice: Subject to any disclaimer, the term of this patent is extended or adjusted under 35 U.S.C. 154(b) by 0 days.

(21) Appl. No.: 16/522,648

(22) Filed: Jul. 26, 2019

(65) Prior Publication Data

US 2020/0015694 A1 Jan. 16, 2020

Related U.S. Application Data

(62) Division of application No. 14/924,239, filed on Oct. 27, 2015, now Pat. No. 10,426,364.

(51) Int. Cl.
| | |
|---|---|
| *A61B 5/04* | (2006.01) |
| *A61B 5/00* | (2006.01) |
| *G16H 50/30* | (2018.01) |
| *G16H 50/20* | (2018.01) |
| *A61B 5/0452* | (2006.01) |
| *G06F 19/00* | (2018.01) |

(52) U.S. Cl.
CPC ........ *A61B 5/04012* (2013.01); *A61B 5/0452* (2013.01); *A61B 5/7203* (2013.01); *A61B 5/7264* (2013.01); *A61B 5/7267* (2013.01); *G06F 19/00* (2013.01); *G16H 50/20* (2018.01); *G16H 50/30* (2018.01)

(58) Field of Classification Search
CPC . A61B 5/04012; A61B 5/7203; A61B 5/7264; A61B 5/7267; G16H 50/30; G16H 50/20
USPC .......................................................... 600/515
See application file for complete search history.

(56) References Cited

U.S. PATENT DOCUMENTS

| | | |
|---|---|---|
| 5,024,225 A | 6/1991 | Fang |
| 5,619,991 A | 4/1997 | Sloane |
| 5,819,007 A | 10/1998 | Elghazzawi |
| 5,907,291 A | 5/1999 | Chen et al. |
| 5,966,692 A | 10/1999 | Langer et al. |
| 6,024,699 A | 2/2000 | Surwit et al. |
| 6,157,850 A | 12/2000 | Diab et al. |

(Continued)

FOREIGN PATENT DOCUMENTS

| | | |
|---|---|---|
| CA | 2466848 A1 | 6/2003 |
| CA | 2975610 A1 | 8/2016 |

(Continued)

OTHER PUBLICATIONS

U.S. Appl. No. 14/924,239, filed Oct. 27, 2015.

(Continued)

*Primary Examiner* — Erin M Piateski
(74) *Attorney, Agent, or Firm* — Eversheds Sutherland (US) LLP; Christopher C. Bolten; Robert D. Ward

(57) ABSTRACT

A method for computerizing delineation and/or multi-label classification of an ECG signal, includes: applying a neural network to the ECG whereby labelling the ECG, and optionally displaying the labels according to time, optionally with the ECG signal.

28 Claims, 4 Drawing Sheets

(56) References Cited

U.S. PATENT DOCUMENTS

| | | |
|---|---|---|
| 6,507,753 B1 | 1/2003 | Xue et al. |
| 6,612,985 B2 | 9/2003 | Eiffert et al. |
| 6,656,125 B2 | 12/2003 | Misczynski et al. |
| 6,694,177 B2 | 2/2004 | Eggers et al. |
| 7,142,907 B2 | 11/2006 | Xue et al. |
| 7,289,844 B2 | 10/2007 | Misczynski et al. |
| 7,941,207 B2 | 5/2011 | Korzinov |
| 8,332,017 B2 | 12/2012 | Tarassenko et al. |
| 8,668,644 B2 | 3/2014 | Ong et al. |
| 8,818,496 B2 | 8/2014 | Dziubinski et al. |
| D717,955 S | 11/2014 | Bishay et al. |
| 8,903,479 B2 | 12/2014 | Zoicas |
| 8,932,220 B1 | 1/2015 | Ong et al. |
| 8,951,193 B2 | 2/2015 | Ong et al. |
| D744,659 S | 12/2015 | Bishay et al. |
| 9,241,650 B2 | 1/2016 | Amirim |
| 9,254,095 B2 | 2/2016 | Galloway et al. |
| 9,295,429 B2 | 3/2016 | Ong et al. |
| 9,339,202 B2 | 5/2016 | Brockway et al. |
| 9,345,414 B1 | 5/2016 | Bardy et al. |
| 9,351,652 B2 | 5/2016 | Dziubinski et al. |
| 9,364,155 B2 | 6/2016 | Bardy et al. |
| 9,408,545 B2 | 8/2016 | Felix et al. |
| 9,408,551 B2 | 8/2016 | Bardy et al. |
| 9,420,957 B2 | 8/2016 | Ong et al. |
| D766,447 S | 9/2016 | Bishay et al. |
| 9,433,367 B2 | 9/2016 | Felix et al. |
| 9,433,380 B1 | 9/2016 | Bishay et al. |
| 9,468,386 B2 | 10/2016 | Braojos Lopez et al. |
| 9,504,423 B1 | 11/2016 | Bardy et al. |
| 9,545,204 B2 | 1/2017 | Bishay et al. |
| 9,545,228 B2 | 1/2017 | Bardy et al. |
| 9,554,715 B2 | 1/2017 | Bardy et al. |
| 9,615,763 B2 | 4/2017 | Felix et al. |
| 9,619,660 B1 | 4/2017 | Felix et al. |
| 9,642,537 B2 | 5/2017 | Felix et al. |
| 9,655,537 B2 | 5/2017 | Bardy et al. |
| 9,655,538 B2 | 5/2017 | Felix et al. |
| 9,700,227 B2 | 7/2017 | Bishay et al. |
| D793,566 S | 8/2017 | Bishay et al. |
| 9,717,432 B2 | 8/2017 | Felix et al. |
| 9,717,433 B2 | 8/2017 | Felix et al. |
| 9,730,593 B2 | 8/2017 | Felix et al. |
| 9,730,641 B2 | 8/2017 | Felix et al. |
| 9,737,211 B2 | 8/2017 | Bardy et al. |
| 9,737,224 B2 | 8/2017 | Bardy et al. |
| D801,528 S | 10/2017 | Bardy et al. |
| 9,775,536 B2 | 10/2017 | Felix et al. |
| 9,788,722 B2 | 10/2017 | Bardy et al. |
| 9,820,665 B2 | 11/2017 | Felix et al. |
| 9,901,274 B2 | 2/2018 | Bishay et al. |
| 9,936,875 B2 | 4/2018 | Bardy et al. |
| 9,955,885 B2 | 5/2018 | Felix et al. |
| 9,955,888 B2 | 5/2018 | Felix et al. |
| 9,955,911 B2 | 5/2018 | Bardy et al. |
| 10,004,415 B2 | 6/2018 | Bishay et al. |
| 10,045,709 B2 | 8/2018 | Bardy et al. |
| 10,052,022 B2 | 8/2018 | Bardy et al. |
| D831,833 S | 10/2018 | Bishay et al. |
| 10,111,601 B2 | 10/2018 | Bishay et al. |
| 10,123,703 B2 | 11/2018 | Bardy et al. |
| 10,154,793 B2 | 12/2018 | Felix et al. |
| D838,370 S | 1/2019 | Bardy et al. |
| 10,165,946 B2 | 1/2019 | Bardy et al. |
| 10,172,534 B2 | 1/2019 | Felix et al. |
| 10,251,575 B2 | 4/2019 | Bardy et al. |
| 10,251,576 B2 | 4/2019 | Bardy et al. |
| 10,264,992 B2 | 4/2019 | Felix et al. |
| 10,265,015 B2 | 4/2019 | Bardy et al. |
| 10,271,755 B2 | 4/2019 | Felix et al. |
| 10,271,756 B2 | 4/2019 | Felix et al. |
| 10,278,603 B2 | 5/2019 | Felix et al. |
| 10,278,606 B2 | 5/2019 | Bishay et al. |
| 10,426,364 B2 | 10/2019 | Rapin et al. |
| 2001/0029338 A1 | 10/2001 | Krishnamachari |
| 2004/0147840 A1* | 7/2004 | Duggirala ............... A61B 8/00 600/437 |
| 2004/0230105 A1* | 11/2004 | Geva ................. A61B 5/04012 600/301 |
| 2005/0101873 A1 | 5/2005 | Misczynski et al. |
| 2005/0113706 A1 | 5/2005 | Prystowsky |
| 2005/0171448 A1 | 8/2005 | Korzinov |
| 2005/0182334 A1 | 8/2005 | Korzinov |
| 2005/0222508 A1* | 10/2005 | Moreno ............. A61B 5/04525 600/509 |
| 2008/0103403 A1 | 5/2008 | Cohen |
| 2008/0132799 A1 | 6/2008 | Xue |
| 2009/0112110 A1 | 4/2009 | Zhang |
| 2009/0192394 A1* | 7/2009 | Guttag ............... A61B 5/02405 600/509 |
| 2010/0268103 A1 | 10/2010 | McNamara |
| 2011/0224565 A1 | 9/2011 | Ong et al. |
| 2011/0257548 A1 | 10/2011 | Dong et al. |
| 2012/0110226 A1 | 5/2012 | Vlach |
| 2013/0116585 A1 | 5/2013 | Bouguerra |
| 2013/0237776 A1 | 9/2013 | Ong et al. |
| 2014/0148714 A1 | 5/2014 | Mamaghanian et al. |
| 2014/0187988 A1 | 7/2014 | Ong et al. |
| 2015/0008802 A1 | 1/2015 | Fukuda |
| 2015/0088020 A1 | 3/2015 | Dreisbach et al. |
| 2015/0088024 A1 | 3/2015 | Sackellares et al. |
| 2015/0190067 A1 | 7/2015 | Prystowsky |
| 2015/0257668 A1 | 9/2015 | Braojos Lopez et al. |
| 2015/0282726 A1 | 10/2015 | Grube et al. |
| 2017/0112401 A1 | 4/2017 | Rapin et al. |
| 2017/0238833 A1 | 8/2017 | Felix et al. |
| 2017/0251948 A1 | 9/2017 | Felix et al. |
| 2017/0258358 A1 | 9/2017 | Bishay et al. |
| 2017/0340290 A1 | 11/2017 | Felix et al. |
| 2017/0367609 A1 | 12/2017 | Bardy et al. |
| 2018/0028144 A1 | 2/2018 | Chen et al. |
| 2018/0177423 A1 | 6/2018 | Bishay et al. |
| 2018/0296118 A1 | 10/2018 | Bishay et al. |
| 2018/0310892 A1 | 11/2018 | Perschbacher et al. |
| 2018/0344191 A1 | 12/2018 | Bardy et al. |
| 2018/0353071 A1 | 12/2018 | Bardy et al. |
| 2019/0059763 A1 | 2/2019 | Shakur et al. |
| 2019/0069794 A1 | 3/2019 | Bardy et al. |
| 2019/0069798 A1 | 3/2019 | Bardy |
| 2019/0069800 A1 | 3/2019 | Bardy et al. |
| 2019/0076023 A1 | 3/2019 | Bardy et al. |
| 2019/0090769 A1 | 3/2019 | Boleyn et al. |
| 2019/0099105 A1 | 4/2019 | Felix et al. |
| 2019/0104961 A1 | 4/2019 | Felix et al. |
| 2019/0117099 A1 | 4/2019 | Bardy et al. |
| 2019/0117107 A1 | 4/2019 | Felix et al. |
| 2019/0133444 A1 | 5/2019 | Bardy et al. |
| 2019/0133486 A1 | 5/2019 | Felix et al. |
| 2019/0167143 A1 | 6/2019 | Li et al. |
| 2019/0223739 A1 | 7/2019 | Rapin et al. |
| 2019/0298204 A1 | 10/2019 | Fontanarava et al. |
| 2020/0015694 A1 | 1/2020 | Rapin et al. |
| 2020/0022604 A1 | 1/2020 | Scabellone et al. |

FOREIGN PATENT DOCUMENTS

| | | |
|---|---|---|
| CA | 2978636 A1 | 9/2016 |
| CN | 101268938 A | 9/2008 |
| CN | 101766484 A | 7/2010 |
| CN | 102188240 A | 9/2011 |
| CN | 102379694 A | 3/2012 |
| CN | 102779234 A | 11/2012 |
| CN | 103110417 A | 5/2013 |
| CN | 103284702 A | 9/2013 |
| CN | 103417209 A | 12/2013 |
| CN | 104463326 A | 3/2015 |
| CN | 104970789 A | 10/2015 |
| CN | 106778685 A | 5/2017 |
| EP | 0 465 241 B1 | 11/1998 |
| EP | 1 179 319 A1 | 2/2002 |
| EP | 1 503 664 A2 | 2/2005 |
| EP | 2 030 565 A1 | 3/2009 |
| EP | 3 048 954 | 8/2016 |

(56) References Cited

FOREIGN PATENT DOCUMENTS

| | | |
|---|---|---|
| EP | 3 048 962 | 8/2016 |
| EP | 3 048 963 | 8/2016 |
| EP | 3 048 964 | 8/2016 |
| EP | 3 144 851 A1 | 3/2017 |
| EP | 3 193 703 | 7/2017 |
| EP | 3 193 704 | 7/2017 |
| EP | 3 193 705 | 7/2017 |
| EP | 3 240 475 | 11/2017 |
| EP | 3 267 881 | 1/2018 |
| EP | 3 267 887 | 1/2018 |
| EP | 3 307 151 | 4/2018 |
| EP | 2 534 597 B1 | 10/2018 |
| KR | 20150020955 A | 2/2015 |
| WO | WO-03/045224 A2 | 6/2003 |
| WO | WO-2006/048881 A2 | 5/2006 |
| WO | WO-2011/115576 A2 | 9/2011 |
| WO | WO-2015/048191 A1 | 4/2015 |
| WO | WO-2015/048194 A1 | 4/2015 |
| WO | WO-2016/145392 A1 | 9/2016 |
| WO | WO-2016/201135 A1 | 12/2016 |
| WO | WO-2017/072250 A1 | 5/2017 |
| WO | WO-2019/038435 A1 | 2/2019 |

OTHER PUBLICATIONS

U.S. Appl. No. 15/771,807, filed Apr. 27, 2018.
U.S. Appl. No. 16/267,380, filed Feb. 4, 2019.
U.S. Appl. No. 16/328,701, filed Feb. 26, 2019.
U.S. Appl. No. 16/367,227, filed Mar. 27, 2019.
Alfonso et al., "ECG Beat Detection Using Filter Banks", Transactions on Biomedical Engineering, 46(2):192-202 (1999).
Almeida et al., "Multilead ECG Delineation Using Spatially Projected Leads From Wavelet Transform Loops", IEEE Transactions on biomedical engineering, 56(8):1996-2005 (2009).
Badilini et al., ECGScan: A Method for Conversion of Paper Electrocardiographic Printouts to Digital Electrocardiographic Files, Journal of Electrocardiology, 38:310-318 (2005).
Bishop, "Pattern Recognition and Machine Learning", Springer, Information Science and Statistics, 2006, ISBN-10: D-387-31073-8.
Boichai et al., "Wavelet-Based ECG Delineation on a Wearable Embedded Sensor Platform", Proceedings of Wearable and Implantable Body Sensor Networks, 2009, pp. 256-261.
Chazal et al., "A Patient-Adapting Heartbeat Classifier Using ECG Morphology and Heartbeat Interval Features", IEEE Transactions on Biomedical Engineering, 53(12):2535-2543 (2006).
Chazal et al., "Automatic classification of heartbeats using ECG morphology and heartbeat interval features", IEEE Transactions on Biomedical Engineering, 51(7):1196-1206 (2004).
Chebil et al., A Novel Method for Digitizing Standard ECG Papers, Proceedings of the International Conference on Computer and Communication Engineering 2008, pp. 1308-1312, May 13-15, 2008, Kuala Lumpur, Malaysia.
Choi et al., "Development of ECG beat segmentation method by combining lowpass filter and irregular R-R interval checkup strategy", Expert Systems with Applications, 37:5208-5218 (2010).
Coast et al., "An Approach to Cardiac Arrhythmia Analysis Using Hidden Markov Models", IEEE transactions on biomedical engineering, 37(9):826-836 (1990).
Cybenko, "Approximation by Superpositions of a Sigmoidal Function", Mathematics of Control, Signals and Systems, 2:303-314 (1989).
Donahue et al., "Long-term Recurrent Convolutional Networks for Visual Recognition and Description", arXiv:1411.4389v3, pp. 1-13, Feb. 17, 2015, Berkeley, CA, USA.
Dr. Dobbs Journal / Neural Nets and Noise Filtering / Jan. 1, 1989, pp. 32.
Dubois et al., "Automatic ECG wave extraction in long-term recordings using Gaussian mesa function models and nonlinear probability estimators", Computer Methods and Programs in Biomedicine, 88:217-233 (2007).

EP Search Report and Written Opinion dated Oct. 15, 2018 in EP Patent Appl. Serial No. 18305376.8.
EP Search Report dated Apr. 13, 2016 in EP Patent Appl. Serial No. 15191769.7.
Fukushima, "Neocognitron: A Self-organizing Neural Network Model for a Mechanism of Pattern Recognition Unaffected by Shift in Position", Biological Cybernetics, vol. 36:193-202 (1980).
Hughes et al., "Markov Models for Automated ECG Interval Analysis," Proceedings of Neural Information Processing Systems, 2004, pp. 611-618, Oxford, UK.
Ieva et al., "Multivariate functional clustering for the morphological analysis of electrocardiograph curves", Journal of the Royal Statistical Society: Series C (Applied Statistics), Blackwell Publishing Ltd, London, UK, 2013, vol. 62, pp. 401-418.
International Search Report & Written Opinion dated Jan. 24, 2017 in Int'l PCT Patent Appl. Serial No. PCT/EP2016/075972.
International Search Report & Written Opinion dated Nov. 21, 2018 in Int'l PCT Patent Appl. Serial No. PCT/EP2018/072912.
Jin et al., "Deep learning research on clinical electrocardiogram analysis", Science China Press, vol. 45(3):398-416 (2015), China, English abstract provided.
Johnson et al., "R-Peak Estimation using Multimodal Lead Switching", Computing in Cardiology 2014, pp. 281-284, Oxford, UK.
Kaur et al., "Comparison of different approaches for removal of Baseline wander from ECG signal", Proceedings published by International Journal of Computer Applications, 2011, pp. 30-36, Sangrur (Pb.), India.
Kiranyaz et al, "Real-Time Patient-Specific ECG Classification by 1-D Convolutional Neural Networks", IEEE Transactions on Biomedical Engineering, 63(3):664-675 (2016).
Kiranyaz et al, "Convolutional Neural Networks for Patient-Specific ECG Classification", 37th Annual International Conference of the IEEE Engineering in Medicine and Biology Society (EMBC). Proceedings IEEE Piscataway, N.J., US, Aug. 2015, pp. 2608-2611.
Krizhevsky et al., "ImageNet Classification with Deep Convolutional Neural Networks", Proceedings of Neural Information Processing Systems, 2012, pp. 1097-1105, Toronto, Canada.
Laguna et al., "A Database for Evaluation of Algorithms for Measurement of QT and Other Waveform Intervals in the ECG", Computers in Cardiology, 24:673-676 (1997).
LeCun et al., "Backpropagation Applied to Handwritten Zip Code Recognition", Neural Computation, 1:541-551 (1989).
Li et al., "Detection of ECG Characteristic Points Using Wavelet Transforms", Transactions on Biomedical Engineering, 42(1):21-28 (1995).
Li et al., Deep Neural Networks Improve Atrial Fibrillation Detection in Detection in Holter: First Results, European Journal of Preventive Cardiology, European Congress on eCardiology & eHealth, Oct. 2016, Abstract, 23 (2S), 41 (2016).
Lin et al., "Beat-to-beat P and T Wave Delineation in ECG Signals Using a Marginalized Particle Filter", Proceedings of EUSIPCO, Toulouse, France, 5 pages (2012).
Lin et al., "P and T Wave Delination and Waveform Estimation in ECG Signals Using a Block Gibbs Sampler", Signal Processing Conference (EUSIPCO), pp. 479-483, Toulouse, France (2012).
Lin et al., "P- and T-Wave Delineation in ECG Signals Using a Bayesian Approach and a Partially Collapsed Gibbs Sampler", IEEE Transactions on Biomedical Engineering, 57(12):2840-2849 (2010).
Long et al., "Fully Convolutional Networks for Semantic Segmentation", Proceedings of Computer Vision and Pattern Recognition, 2015, pp. 3431-3440, Berkeley, CA, USA.
Martinez et al., "A Wavelet-Based ECG Delineator: Evaluation on Standard Databases" IEEE transactions on biomedical engineering, 51(4):570-581, Zaragoza, Spain.
Matan et al., "Multi-Digit Recognition Using a Space Displacement Neural Network", Neural Information Processing Systems, Morgan Kaufmann, 1992, pp. 488-495, Holmdel, NJ USA.
Megriche, et al., On the Analysis of a Compound Neural Network for Detecting Atrio Ventricular Heart Block (AVB) in a ECG Signal, International Journal of Medical, Health, Biomedical, Bioengineering and Pharmaceutical Engineering, 2(3):68-78 (2008).

(56) References Cited

OTHER PUBLICATIONS

Megriche, et al., On the Analysis of a Compound Neural Network for Detecting Atrio Ventricular Heart Block (AVB) in an ECG Signal, International Journal of Biological and Life Sciences, 4(1):1-11 (2008).

Mnih et al., "Recurrent Models of Visual Attention", Google DeepMind, arXiv:1406.6247v1, pp. 1-12, Jun. 24, 2014.

Noda et al., "Audio-visual speech recognition using deep learning", Appl. Intell., 42:722-737 (2015).

Nowlan et al., "A Convolutional Neural Network Hand Tracker", Advances in Neural Information Processing Systems 7, Morgan Kaufmann, 1995, pp. 901-908, Synaptics, Inc. San Jose, CA USA.

Pan et al., "A Real-Time QRS Detection Algorithm", IEEE Transactions on Biomedical Engineering, vol. BME-32, No. 3, Mar. 1985, pp. 230-236, Shanghai, P.R. of China.

Pigoli et al., "Wavelets in functional data analysis: Estimation of multidimensional curves and their derivatives", Computational Statistics and Data Analysis, 56:1482-1498 (2012), Politecnico di Milano, Italy.

Portet, P wave detector with PP rhythm tracking: Evaluation in different arrhythmia contexts, Physiological Measurement, Institute of Physics: Hybrid Open Access, 29:141-155 (2008), Scotland, UK.

Prineas et al., "The Minnesota Code Manual of Electrocardiographic Findings", Springer, Second Edition, ISBN D78-1-84882-777-6, 2009, Minneapolis, Minnesota, US.

Ravichandran, et al., Novel Tool for Complete Digitization of Paper Electrocardiography Data, IEEE Journal of Translational Engineering in Health and Medicine, Medical Imaging and Diagnostic Radiology, vol. 1, 7 pages, Jun. 2013.

Rodrigues et al,."A Neural Network Approach to ECG Denoising", CoRR, Dec. 2012, abs/1212.5217, pp. 1-15, Caparica, Portugal.

Rosenblatt, "The Perceptron: A Probabilistic Model for Information Storage and Organization in the Brain", Psychological Review, 65(6):386-408 (1958), Buffalo, NY, USA.

Russakovsky et al., "ImageNet Large Scale Visual Recognition Challenge", arXiv:1409.0575v3, pp. 1-43, Jan. 30, 2015, Stanford, CA, USA.

Saini et al., "Automated ECG Delineation using Machine Learning Algorithms", International Congress on Electrocardiology, 2014, pp. 1-4, Jalandhar, India.

Schluter et al., "Improved Musical Onset Detection With Convolutional Neural Networks", EEE International Conference on Acoustics, Speech, and Signal Processing ICASSP 2014,99 1-5, Linz, Austria.

Shen et al., "Multi-level ECG Classification Based on Independent Component Analysis and Support Vector Machine," Biomedical Engineering and Informatics (BMEI), 3:960-964 (2010).

Simonyan et al., Very Deep Convolutional Networks for Large-Scale Image Recognition, Published as a conference paper at ICLR, Apr. 10, 2015.

Smith et al., Improved Interpretation of Atrial Dyshrthmias by a New Neural Network Electrocardiogram Interpretation Algorithm, Society for Academic Emergency Medicine Abstracts, 24(S1), S235 (2017).

Statement of Validation and Accuracy for the Glasgow 12-Lead ECG Analysis Program, Physio Control, Mar. 2009, Redmond, WA USA.

Vaessen, "An approach to ECG Delineation using Wavelet Analysis and Hidden Markov Models", Universiteit Maastricht Institute of Instrument Development Engineering & Evaluation Master Thesis, Sep. 2006.

Zeiler, Matthew D., ADADELTA: An Adaptive Learning Rate Method, dated Dec. 22, 2012, prepared while at Google Inc., USA. (arXiv: 1212.5701 [cs.LG].

Zhang et al., "Improving object detection with deep convolutional networks via bayesian optimization and structured prediction", Computer Vision Foundation CVPR2015, pp. 249-258, Zhejiang, China.

Zheng et al., "Time Series Classification Using Multi-Channels Deep Convolutional Neural Networks", Web-Age information Management, 8485:298-310 (2014), Switzerland.

International Search Report & Written Opinion dated Aug. 1, 2019 in Int'l PCT Patent Appl. Serial No. PCT/IB2019/052517 (0510 PCT).

International Search Report & Written Opinion dated Jun. 4, 2020 in Int'l PCT Patent Appl. Serial No. PCT/IB2020/050850 (0710 PCT).

* cited by examiner

AUTOMATIC METHOD TO DELINEATE OR CATEGORIZE AN ELECTROCARDIOGRAM

CROSS-REFERENCE TO RELATED APPLICATIONS

This application is a divisional application of U.S. patent application Ser. No. 14/924,239, filed Oct. 27, 2015, now U.S. Pat. No. 10,426,364, issued Oct. 1, 2019, the entire contents of which are incorporated herein by reference.

FIELD OF INVENTION

The present invention relates to temporal signal analysis, preferably ECG analysis, using at least one neural network.

BACKGROUND OF INVENTION

The electrocardiogram (ECG) is a graphic representation of the electrical activity of the heart. It is recorded from the body surface using a number of electrodes placed in specific predefined areas. It is considered as a fundamental tool of clinical practice. It is a simple, non-invasive exam that can be performed by any health professional. Placing the electrodes is not considered as a medical procedure, yet in some countries, the prescription of the ECG by a doctor is essential for it to be performed. The ECG constitutes the first step in cardiovascular diseases (CVD) diagnosis, and is used multiple times throughout the life of a CVD patient, CVD constitute the first global cause of death.

An ECG is composed of multiple temporal signals, called lead signals, such as the standard 12-lead ECG shown in FIG. 1. An ECG displays repeating patterns usually comprising a P-wave, a QRS complex and a T-wave, respectively corresponding to the depolarization of the atria, depolarization of the ventricles and repolarization of the ventricles. These waves and complex are shown in FIG. 2, which focuses on a couple of beats in one lead signal.

The ECG allows for the detection of many anomalies, which often in turn point to specific CVD. It is estimated that about 150 measurable anomalies can be identified on ECG recordings today. However, without specific expertise and/or regular training, only a small portion of these anomalies can be easily spotted. Unfortunately, today, it is estimated that only one third of ECGs are performed in settings where cardiology expertise is readily available.

In order to make ECO interpretation simpler and assist non-specialists, two alternatives exist today, but neither fully satisfy the needs of health professionals:

Telecardiology centers, where an interpretation of an ECG sent by a non-specialist is delivered either by cardiologists or by specialized ECG technicians. Their interpretations am of high quality but are slow and expensive to obtain.

Prior art automated ECG interpretation softwares, which are mainly developed by ECG device manufacturers. They provide low quality interpretation (false alarms are very frequent) but deliver them in seconds.

Prior art automated ECG interpretation softwares can provide two types of information about an ECG signal:
the temporal locations of each wave, called its "delineation", and/or
a classification of the ECG as normal/abnormal or labeling its anomalies.

Two main approaches are used for the delineation of ECG signals.

The first one is based on multiscale wavelet analysis. This approach looks for wavelet coefficients reaching predefined thresholds at well-chosen scales (Martinez et al, IEEE transactions on biomedical engineering. Vol. 51, No. 4, April 2004, 570-581, Almeida et al., IEEE transactions on biomedical engineering, Vol. 56, No. 8, August 2009, pp 1996-2005, Boichat et al., Proceedings of Wearable and Implantable Body Sensor Networks, 2009, pp 256-261, U.S. Pat. No. 8,903,479, 2014 Dec. 2, Zoicas et al.). The usual process is to look for QRS complexes, and then look for P waves on the signal before the complexes, and after them for T waves. This approach can only handle a single lead at a time, sometimes using projection to one artificial lead (US 2014/0148714-2014-05-29, Mamaghanian et al). This computation is made very unstable by the use of thresholds. The approach is also limited as it can neither deal with multiple P waves nor with "hidden" P waves. A hidden P wave is a P wave which occurs during another wave or complex, such as for example during a T wave.

The second one is based on Hidden Markov Models (HMM). This machine learning approach considers that the current state of the signal (whether a sample is either part of a QRS complex, a P wave, a T wave or no wave) is a hidden variable that one wants to recover (Coast et al., IEEE transactions on biomedical engineering, Vol. 37, No. 9, September 1990, pp 826-836, Hughes et al., Proceedings of Neural Information Processing Systems, 2004, pp 611-618, U.S. Pat. No. 8,332,017, 2012 Dec. 11, Trassenko et al). To this end, a representation of the signal must be designed using handcrafted "features", and a mathematical model must be fitted for each wave, based on these features. Based on a sufficient number of examples, the algorithms can learn to recognize each wave. This process can however be cumbersome since the feature design is not straightforward, and the model, usually Gaussian, is not well adapted. Also, none of these works has considered the situation of hidden P waves.

As for anomalies and/or CVD detection, most algorithms use rules based on temporal and morphological indicators computed using the delineation: PR, RR and QT intervals, QRS width, level of the ST segment, slope of the T wave, etc. . . . These rules such as the Minnesota Code (Prineas et al., Springer, ISBN 978-1-84882.777-6, 2009) were written by cardiologists. However, they do not reflect the way the cardiologists analyze the ECGs and are crude simplifications. Algorithms such as the Glasgow University Algorithm are based on such principles (Statement of Validation and Accuracy for the Glasgow 12-Lead ECG Analysis Program, Physio Control, 2009).

More advanced methods use learning algorithms, and are built using a diagnosis and an adequate representation for each ECG they learn from; however, in these methods, once again, it is necessary to seek a representation of the raw data into a space that preserves the invariance and stability properties. Indeed, an ECG signal varies significantly from one patient to another. It is therefore extremely difficult for an algorithm to learn how to discriminate different diseases by simply comparing raw data. A representation which drastically limits this interpatient variability while preserving the invariance within the same disease class must be chosen.

In order to solve the above-mentioned issues, the Applicant turned to architectures called neural network. Such architectures have been intensively studied in the field of imaging (Russakovsky et al., arXiv:1409.0575v3, 30 Jan. 2015), but limitations arose when, very recently, the first scientific teams attempted to apply them to ECGs (Zheng et al., Web-Age Information Management, 2014, Vol. 8485, pp 298-310, Jin and Dong, Science China Press, Vol. 45, No 3, 2015, pp 398-416). Indeed, these prior arts only limit the classification to an attempt to identify normal ECG versus abnormal ECG, or to perform a beat-to-beat analysis. The beat-to-beat analysis adds a preprocessing step while reducing the ability of the neural network to learn some anomalies: rhythm disorders, for example, cannot be identified from the observation of a single beat. In fact, these algorithms only consider single-label classification whereas multi-label classification is essential in ECG interpretation, since one ECG can present several anomalies.

Thus, there is a need for computerized algorithms able to analyze ECG that can:
  carry out the analysis without constraints from the ECG recording duration;
  carry out the analysis without the need for beat-by-beat processing, or feature extraction;
  obtain the delineation of the signal, including identification of hidden P waves;
  provide a multi-label classification directly from a full ECG, possibly exhibiting multiple labels;
  be fast, stable and reliable.

SUMMARY

To address the above issues in ECG analyses, the Applicant developed two techniques based on convolutional neural networks.
  A fully convolutional neural network which first gives a dense prediction of the probability of presence of each wave on each time stamp of the ECG, then post-processes the signal to produce its delineation. This novel approach of the delineation, using convolutional networks, allows the processing of ECGs of any duration, analyzing all types of waves in the same way, without being constrained by their positions.
  A recurrent convolutional neural network which predicts directly multiple labels on the whole ECG signal. This structure allows the processing of an ECG of any duration, and takes into account the time dynamic in its analysis. It results in a fixed format output (multi-labels).

Thus, the present invention relates to a method for computerizing the delineation of an ECG signal, comprising: applying a fully convolutional neural network NN1 to said ECG, whereby the fully convolutional neural network NN1 reads each time point of the ECG signal, analyzes temporally each time point of the ECG signal, assigns to each time point of the ECG a score for at least the following: P-wave, QRS complex, T-wave, and then, optionally and whenever necessary, displaying the scores according to time, optionally with the ECG signal.

According to an embodiment, the method further comprises a pre-treatment step, wherein the pre-treatment comprises denoising and removing the baseline of the ECG signal as well as expressing it at a chosen frequency prior to the application of NN1.

According to an embodiment, the method further comprises a post-treatment step, so as to produce the time points of the beginning and the end of each wave in the ECG signals, called the onsets and offsets.

The invention also comprises a software comprising a trained neural network for delineation of an ECG signal. The invention also comprises a computer device comprising a software implementing a method for delineation of an ECG signal, comprising applying a fully convolutional neural network NN1 to said ECG, as described above.

This invention also includes a method for computerizing multi-label classification of an ECG signal, comprising applying a convolutional neural network NN2 to said ECG, whereby the recurrent neural network NN2 reads each time point of the ECG signal, analyzes each time point of the signal, computes scores for each anomaly and allots to an ECG at least one disease-related label, and then, optionally, displaying the labels, preferably in the form of a list of detected anomalies.

According to an embodiment, the method further comprises a pre-treatment step, wherein the pre-treatment comprises denoising and removing the baseline of the ECG signal as well as expressing it at a chosen frequency prior to the application of NN2.

According to an embodiment, the method further comprises a post-treatment step, so as to produce the onset and offset of each wave in the ECG signal.

The invention also comprises a software comprising a trained neural network for multi-label classification of an ECG signal. The invention also comprises a computer device comprising a software implementing a method for multi-label classification of an ECG signal, comprising applying a recurrent neural network NN2 to said ECG, as described above.

Furthermore, the invention also includes a method for computerizing delineation and multi-label classification of an ECG signal, comprising applying a trained recurrent neural network NN3 to said ECG, whereby the recurrent neural network NN3 reads each time point of the ECG signal, analyzes temporally each time point of the signal, assigns a score for at least the following: P-wave, QRS complex, T-wave, no wave; computes scores for each anomaly, and then, optionally, displaying the interval labels according to time and the anomaly scores, preferably in the form of a list of detected, optionally with the ECG signal.

According to an embodiment, the method further comprises a pre-treatment step, wherein the pre-treatment comprises denoising and removing the baseline of the ECG signal as well as expressing it at a chosen frequency prior to the application of NN3.

According to an embodiment, the method further comprises a post-treatment step, so as to produce the onset and offset of each wave in the ECG signal.

The invention also comprises a software comprising a trained neural network for delineation and multi-label classification of an ECG signal. The invention also comprises a computer device comprising a software implementing a method for delineation and multi-label classification of an ECO signal, comprising applying a neural network NN3 to said ECG, as described above.

DETAILED DESCRIPTION

The present invention relates to temporal signal analysis, preferably ECG analysis, using at least one convolutional neural network.

The framework used here is the one of supervised learning. The aim of supervised learning is to predict an output vector Y from an input vector X. In the Applicant embodiment, X is an ECG (a multivariate signal) as a matrix of size m×n. As for Y, in the Applicant embodiment, it can be:
  the delineation, providing a score for each sample of X to be part of one of the different waves as a matrix of size p×n;
  the scores for each anomaly as a vector of size q;

the set composed of both the delineation and the vector of scores.

The problem of supervised learning can also be stated as follows: designing a function f such that for any input X, $f(X) \approx Y$. To this end, the function f is parameterized, and these parameters are "learned" (parameters are optimized with regards to an objective loss function, for example, by means of a gradient descent (Bishop, Pattern Recognition and Machine Learning, Springer, 2006, ISBN-10: 0-387-31073-8).

A neural network is a particular type of function f, aiming at mimicking the way biological neurons work. One of the most basic and earliest neural network is the perceptron (Rosenblatt, Psychological Review, Vol. 65, No. 6, 1958, pp 386-408). From the input X, it computes linear combinations (i.e. weighted sums) of the elements of X through a multiplication with a matrix W, adds an offset b, and then applies a non-linear function σ, such as for instance a sigmoid, on every element of the output:

$$f(X)=\sigma(WX+B)$$

The parameters which are learned in a perceptron are both W and B. In practice, more general neural networks are just compositions of perceptrons:

$$f(X)=\sigma_n(W_n \ldots \sigma_n(W_1 X+B_1)+B_n)$$

The output of a perceptron can be sent as input to another one. The input, the final output, and the intermediate states are called layers. The intermediate ones are more specifically called hidden layers, since only the input and the final output are observed. For instance, a neural network with one hidden layer can be written as:

$$f(X)=\sigma_2(W_2\sigma_1(W_1 X+B_1)+B_2)$$

Such a network is shown in a graphic form as an example in FIG. 3. The vector X enters the network as the input layer, each element of the hidden layer is then computed from linear combinations of all elements of X (hence all the links), and the element of the output layer are then computed from linear combinations of all elements of the hidden layer.

It has been shown that neural networks in their general form are able to approximate all kinds oft functions (Cybenko, Math, Control Signals Systems, Vol. 2, 1989, pp 303-314). The term "deep learning" is used when a neural network is composed of many layers (though the threshold is not perfectly defined, it can be set to about ten). This field arose mostly in the last decade, thanks to recent advances in algorithms and in computation power.

Convolutional neural networks are a particular type of neural networks, where one or more of the matrices $W_i$ which are learned do not encode a full linear combination of the input elements, but the same local linear combination at all the elements of a structured signal such as for example an image or, in this specific context, an ECG, through a convolution (Fukushima, Biol. Cybernetics, Vol. 36, 1980, pp 193-202, LeCun et al., Neural Computation, Vol. 1, 1989, pp 541.551). An illustration of a convolutional neural network is shown in FIG. 6. Most convolutional neural networks implement a few convolutional layers and then standard layers so as to provide a classification. A network which only contains convolutional networks is called a fully convolutional neural network. Finally, a recurrent convolutional neural network is a network composed of two sub-networks: a convolutional neural network which extracts features and is computed at all time points of the ECG, and a neural network on top of it which aggregates in time the outputs of the convolutional neural network. An illustration of a recurrent convolutional neural network is provided in FIG. 7.

As mentioned above, an ECG is represented as a matrix of real numbers, of size m×n. The constant m is the number of leads, typically 12, though networks could be taught to process ECG with any number of leads. The number of samples n provides the duration of the ECG n/f, with f being the sampling frequency of the ECG. A network is trained for a given frequency, such as for example 250 Hz or 500 Hz or 1000 Hz, though any frequency could be used. A same network can however process ECG of any length n, thanks to the fact that it is fully convolutional in the embodiment of the delineation, or thanks to the use of a recurrent neural network in the embodiment of the anomaly network.

In both the delineation and the multi-label classification embodiment s, networks are expressed using open softwares such as for example Theano. Caffe or Torch. These tools provide functions for computing the output(s) of the networks and for updating their parameters through gradient descent. The exact structure of the network is not extremely important as long as they are deep structures: fully convolutional in the situation of the delineation network (Long et al., Proceedings of Computer Vision and Pattern Recognition, 2015, pp 3431-3440), and convolutional (Krizhevsk et al., Proceedings of Neural Information Processing Systems, 2012, pp 1097-1105), potentially recurrent in the situation of the multi-label classification network (Donahue et al., arXiv: 1411.4389v3, 17 Feb. 2015 and Mnih et al., arXiv: 1406.6247v1, 24 Jun. 2014). The 2D convolutional layers which were used on images are then easily converted into 1D convolutional layers in order to process ECO signals.

This invention also pertains to a method for manufacturing a neural network for delineation of an ECG, by training it.

The training phase of the neural networks in the embodiment of delineation consists in the following steps:
 taking one ECG from a dataset containing ECGs and their known delineation; the ECG being expressed as a matrix of size m×n with m fixed and at a predefined frequency;
 expressing the delineation of this ECG under the form of a matrix y of size p×n where p is the number of annotated types of wave; typically p=3, so as to identify P waves, QRS complexes, and T waves; annotations are usually expressed as lists of wave with their start and end points such as for example: (P, 1.2s, 1.3s). (QRS 1.4s 1.7s), (T, 1.7, 2.1), (P, 2.2, 2.3); in this example, the first row of y, corresponding to P waves, will be 1 for samples corresponding to times between 1.2 and 1.3s, and between 2.2 and 2.4s, and 0 otherwise; row 2 will correspond to QRS complexes and row 3 to T waves;
 computing the output of the network for this ECG;
 modifying the parameters of the network so as to decrease a cost function comparing the known delineation and the output of the network; a cross-entropy error function is used so as to allow for multi-labeling (allowing for multiple waves at a given instant); this minimization can be done though a gradient step
 repeating steps 1 to 4 at least once for each ECG of the dataset;
 recovering the neural network.

This invention also provides a method for manufacturing a neural network for the categorization of an ECG signal, by training it.

In a multi-label classification, the manufacturing/training process includes the following steps:

taking one ECG from a dataset containing ECGs and their known anomaly labels; the ECG must be expressed as a matrix of size m×n with m fixed and at a predefined frequency;

expressing the anomalies as a vector of size q, with q the number of anomalies to identify; this vector could be [0; 1; 0; 0; 1; 0; 0; 0] for q=8; a 1 is set in the vector at the index corresponding to the anomalies which are present: in the above example, the ECG exhibits two anomalies;

computing the output of the network for this ECG;

modifying the parameters of the network so as to decrease a cost function comparing the known label vector and the output of the network; a cross-entropy error function is used so as to allow for multi-labeling (allowing for multiple anomalies for an ECG); this minimization can be done though a gradient step;

repeating steps 1 to 4 at least once for each ECG of the dataset;

recovering the neural network.

This invention also provides a method for manufacturing a neural network for both the delineation and the categorization of an ECG signal, by training it.

In the embodiment of the combination of delineation with multi-label classification, the manufacturing process includes the following steps:

taking one ECG from a dataset containing ECGs and their known anomaly labels; the ECG must be expressed as a matrix of size m×n with m fixed and at a predefined frequency;

expressing the anomalies as a vector of size q, with q the number of anomalies to identify; this vector could be [0; 1; 0; 0; 1; 0; 0; 0] for q=8; a 1 is set in the vector at the index corresponding to the anomalies which are present: in the above example, the ECG exhibits two anomalies;

expressing the delineation of this ECG under the form of a matrix Y of size p×n where p is the number of waves to identify; typically p=3, so as to identify P waves, QRS waves, and T waves; annotations are usually expressed as lists wave type with their start and end points such as for example: (P, 1.2s, 1.3s), (QRS 1.4s 1.7s), (T, 1.7, 2.1), (P, 2.2, 2.3); in this example, the first row of Y, corresponding to P waves, will be 1 for samples corresponding to times between 1.2 and 1.3s, and between 2.2 and 2.4s, and 0 otherwise; row 2 will correspond to QRS complexes and row 3 to T waves;

computing both outputs of the network for this ECG;

modifying the parameters of the network so as to decrease the sum of a cost function comparing the known label vector and one of the output of the network, and a cost function comparing the delineation and the other output; cross-entropy error functions are used to allow for multi-labeling (allowing for multiple anomalies for an ECG as well as multiple waves at any time point); this minimization can be done though a gradient step;

repeating steps 1 to 4 at least once for each ECG of the dataset;

recovering the neural network.

This invention also pertains to a method and a device for delineation of an ECG signal, implementing a fully convolutional neural network trained for delineation of an ECG signal as described above.

As a basis, it shall be understood that the ECG is expressed as a matrix X of size m×n at the frequency used for training the networks. The ECG is used as input of the trained neural network.

The neural network then reads each time point of the ECG signal, analyzes spatio-temporally each time point of the ECG signal, assigns a temporal interval score to anyone of at least the following: P-wave, QRS complex, T-wave. It then recovers the output of the neural network, as a matrix Y of size p×n. An example is shown in FIG. 4: the first signal shows one of the leads of the ECG (to help the visualization), the following 3 signals are the outputs of the network, providing scores for P waves, QRS waves and T waves. As it can be seen, these scores are synchronized with the appearance of the aforementioned waves in the signal.

In a preferred embodiment, the neural network provides scores at each time point as a matrix Y, and a post-processing allows the allocation of each time point to none, single, or several waves, and provides the onset and offset of each of the identified waves. For instance, a sample can be affected to the waves for which the score on the corresponding row of Y is larger than 0.5. This provides a delineation sequence of type (P, 1.2s, 1.3s), (QRS 1.4s 1.7s), (T, 1.7s, 2.1s), (P, 2.2s, 2.3s), as recorded in the annotations.

In an embodiment, finally, the labels may be optionally displayed according to time, optionally with the ECG signal.

This invention also pertains to a method and a device for multi-label classification of an ECG signal, implementing Long-term Recurrent Convolutional Networks (LRCN, (Donahue et al., arXiv:1411.4389v3, 17 Feb. 2015). These neural networks are trained for multi-label classification of an ECG signal as described above.

As a basis, it shall be understood that the ECG is expressed as a matrix of size m×n at the frequency used for training the networks. Then, the ECG is used as input of the trained neural network.

The neural network then reads each time point of the ECG signal, analyzes temporally each time point of the ECG signal, computes a score for each anomaly, recovers the output of the neural network, and optionally displays the labels.

In a preferred embodiment, the neural network recovers the output as a vector of size q. This vector contains scores for the presence of each anomaly.

According to an embodiment, the neural network displays the list of found anomalies as the elements for which the score in the vector are higher than a predefined threshold, typically 0.5.

This invention also pertains to a method and a device for delineation and multi-label classification of an ECG signal, implementing a neural network trained for delineation and multi-label classification of an ECG signal as described above.

As a basis, it shall be understood that the ECG is expressed as a matrix of size m×n at the frequency used for training the networks. Then, the ECG is used as input of the trained neural network.

The neural network then reads each time point of the ECG signal, analyzes temporally each time point, assigns a temporal score to all of the following at least: P-wave, QRS complex, T-wave. It then computes a score for each anomaly, recovers both the outputs of the neural network: the first as a matrix y of size p×n, providing scores for at least P waves, QRS waves and T waves; and the second as a vector of size q, said vector containing scores for the presence of each anomaly.

In a preferred embodiment, a post-processing of the delineation output allows to affect each time point to none, single, or several waves, and provides the onset and offset of each of the identified waves. For instance, a sample can be affected to the waves for which the score on the corresponding row of Y is larger than 0.5. This provides a delineation sequence of type (P, 1.2s, 1.3s), (QRS 1.4s 1.7s), (T, 1.7s, 2.1s), (P, 2.2s, 2.3s), as recorded in the annotations.

According to an embodiment, the neural network displays the list of found anomalies as the elements for which the score in the vector are higher than a predefined threshold, typically 0.5, as well as the delineation, optionally with the ECG signal.

The invention also comprises a computer device implemented software comprising a trained neural network for delineation of an ECG signal. The invention also comprises a device, such as f r example a cloud server, a commercial ECG device, a mobile phone or a tablet, comprising a software implementing a method for delineation, multi-label classification or both, of an ECG signal, as described above.

According to an embodiment of the invention, a step to prepare the signal and create input variables for classification is further carried out ("pre-treatment"). The purpose of this pre-treatment is to remove the disturbing elements of the signal such as for example noise and baseline, low frequency signal due to respiration and patient motion, in order to facilitate classification. For noise filtering, a multivariate approach functional analysis proposed by (Pigoli and Sangalli, Computational Statistics and Data Analysis, vol. 56, 2012, pp 1482-1498) can be used. The low frequencies of the signal corresponding to the patient's movements may be removed using median filtering as proposed by (Kaur et al., Proceedings published by International Journal of Computer Applications, 2011, pp 30-36).

According to an embodiment of the invention, a post-treatment step is added, so as to produce the onset and offset of each wave in the ECG signal.

This invention brings to the art a number of advantages, some of them being described below:

- The input of the networks are one or multilead ECG signals with variable length, possibly preprocessed so as to remove noise and baseline wandering due to patients movements, and express the signal at a chosen frequency.
- The output of a classification network is a vector of scores for anomalies. These are not classification scores since one ECG can present several anomalies. For example, the output of such network could be a vector [0.98; 0.89; 0.00; . . . ] with the corresponding labels for each element of the vector (Right Bundle Branch Bloc; Atrial Fibrillation; Normal ECG; . . . ). Scores are given between a scale of [0, 1] and the example output vectors therefore indicates a right bundle branch block and atrial fibrillations. A recurrent neural network architecture can be added on the top of the convolutional network (Donahue et al., arXiv:1411.4389v3, 17 Feb. 2015 and Mnih et al., arXiv:1406.6247v1, 24 Jun. 2014). In this way, the convolution network acts as a pattern detector whose output will be aggregated in time by the recurrent network.
- The output of the delineation network is a set of signals spanning the length of the input ECG signal, providing the score for being in P wave, a QRS complex, a T wave and potentially other types of waves such as for example premature ventricular complexes, flutter waves, or U waves. An example of output signals is provided in FIG. 5.
- The delineation network is not limited to recovering at most one wave at each time point and therefore can identify several waves at any time point, such as for instance hidden P waves, No works applying convolutional networks to the delineation have been made so far.

The underlying structure of the networks is not fundamental as long as it is a recurrent network for the multi-label classification network and a fully convolutional network for the delineation network. One can use a structure such as RLCN (Donahue et al., arXiv:1411.4389v3, 17 Feb. 2015 and Mnih et al., arXiv:1406.6247v1, 24 Jun. 2014) for classification and a network similar as the one in (Long et al., Proceedings of Computer Vision and Pattern Recognition, 2015, pp 3431-3440) for delineation. In both embodiments, convolutional layers must be modified as 1D convolutions instead of 2D convolutions.

A hybrid network, sharing the first convolutional layers and diverging so as to provide both the delineation as one output, and the multi-label classification as another output is also used. This combination has the advantage of being able to produce a multi-label classification helped by the identification of the ECG waves.

EXAMPLES

The present invention is further illustrated by the following examples.

Example 1: Training for Delineation

This training was performed on 630 ECGs and the network evaluated on about 900 beats from 70 different patients which were not used for the training phase. The false positive rate was 0.3% for QRS complexes and T waves detection and their false negative rate was 0.2%, They were respectively 5.4% and 4.2% for P waves. The precision of the wave onsets (beginnings) and offsets (ends) are detailed below:

| Point | Standard Deviation (ms) | Bias (ms) |
| --- | --- | --- |
| P wave start | 11.2 | −1.6 |
| P wave end | 11.2 | −4.0 |
| QRS complex start | 6.3 | −2.1 |
| QRS complex end | 3.9 | −1.1 |
| T wave end | 16.1 | −4.6 |

Compared with state-of-the art algorithms, the precision was improved. In FIG. 5 for instance, the ECG exhibits an atrioventricular block which means that the P waves and the QRS complexes are completely decoupled. In this example, the P waves are regular and QRS complexes happen at random times. One can observe in this example that the algorithm correctly found two P waves between the first QRS complex and the second QRS complex, while most algorithms would not be able to find them since they look for only one P wave before each complex. The last P wave also starts before the end of the last T wave, adding complexity. Other algorithms would not have been able to find this hidden wave.

Example 2: Training for Multi-Label Classification

A network has been trained using about 85,000 ECGs and has been evaluated on a Dataset including 20,000 patients which were not used in the training phase. For the evaluation purpose, the multi-label classification obtained was simplified to normal (no anomaly)/abnormal if need be. The results in terms of accuracy, specificity and sensitivity were the following:

| Accuracy | Specificity | Sensitivity |
|---|---|---|
| 0.91 | 0.88 | 0.92 |

A graphical representation of how a standard multi-label is used on ECGs is displayed in FIG. 6. The ECG is given as input to the network, which aggregates the information locally and then combines it layer by layer to produce a high-level multi-label classification of the ECG, in this example correctly recognizing atrial fibrillations and a right bundle branch block. Such networks however take a fixed size as input and the process must be reproduced at different locations so as to analyze the whole signal. FIG. 7 is an example of a graphic representation of a recurrent neural network which overcomes this issue. This type of network is made from a standard convolutional network computed at all possible locations of the signal, and on top of which comes another network layer which aggregates the information. In this example, the network correctly recognizes a premature ventricular complex (PVC, the fifth and largest beat) in the first part of the signal while the second pan of the signal is considered as normal. The aggregated output is therefore PVC since this ECG has an anomaly and cannot therefore be considered as normal.

Example 3

In another embodiment, the applicant combines features described above in examples 1 and 2. Such combination enables to combine the advantages of both networks in a unique network, providing similar results for both the delineations and the multi-label classifications.

Figure 1:
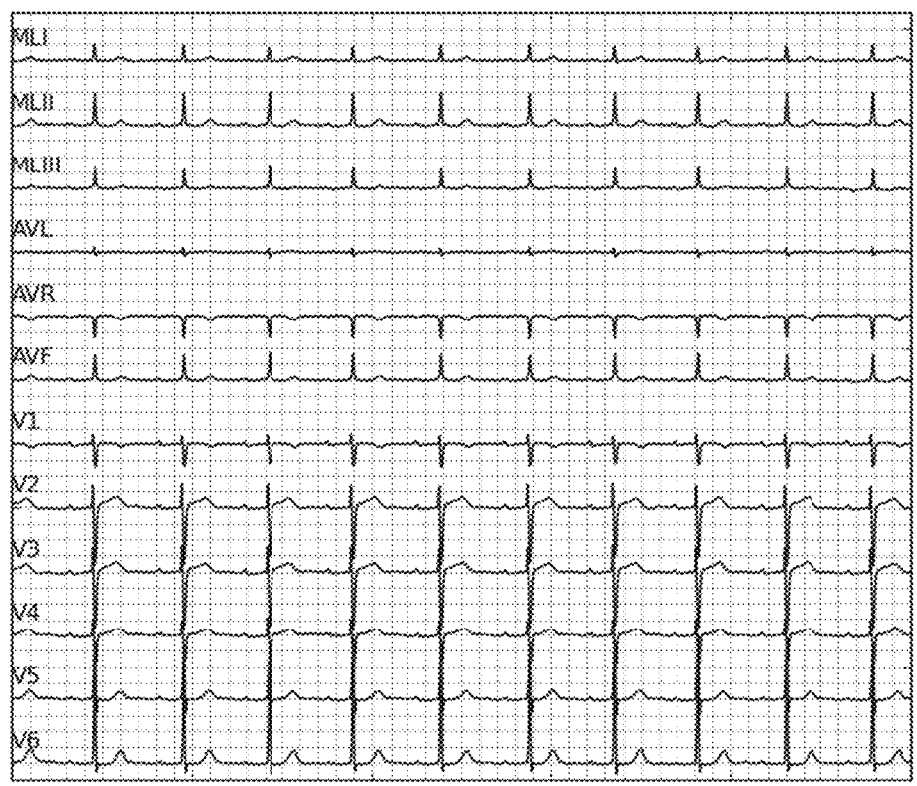
FIG. 1 is a photo of an ECG.
Figure 2:
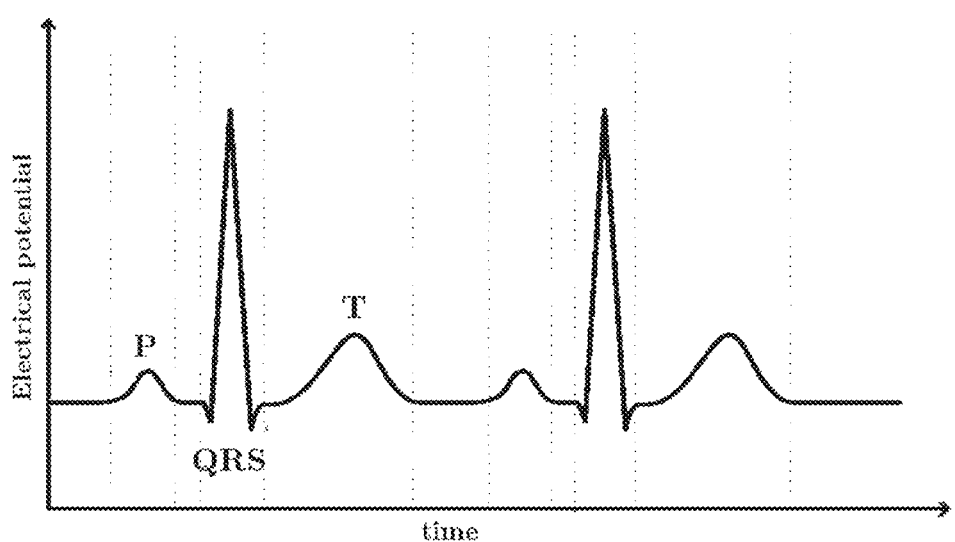
FIG. 2 is a schematic representation of a normal EGG, with the P wave, the QRS complex/wave comprising the Q, R, S and J points, and the T wave.
Figure 3:
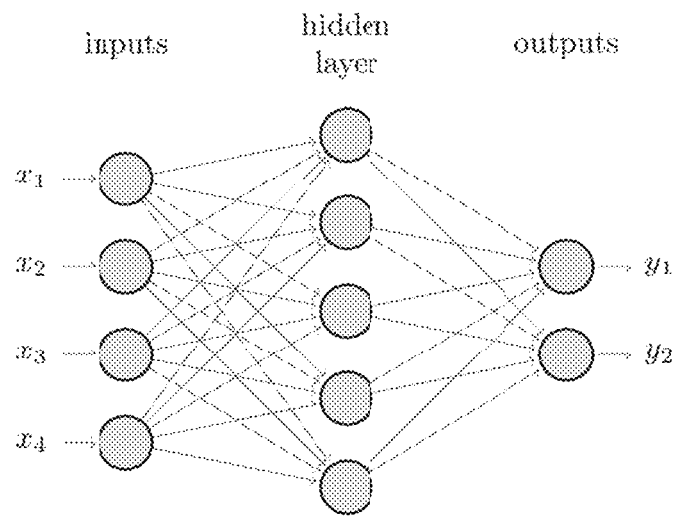
FIG. 3 is an example of structure for a basic neural network with no convolutional layer.
Figure 4:
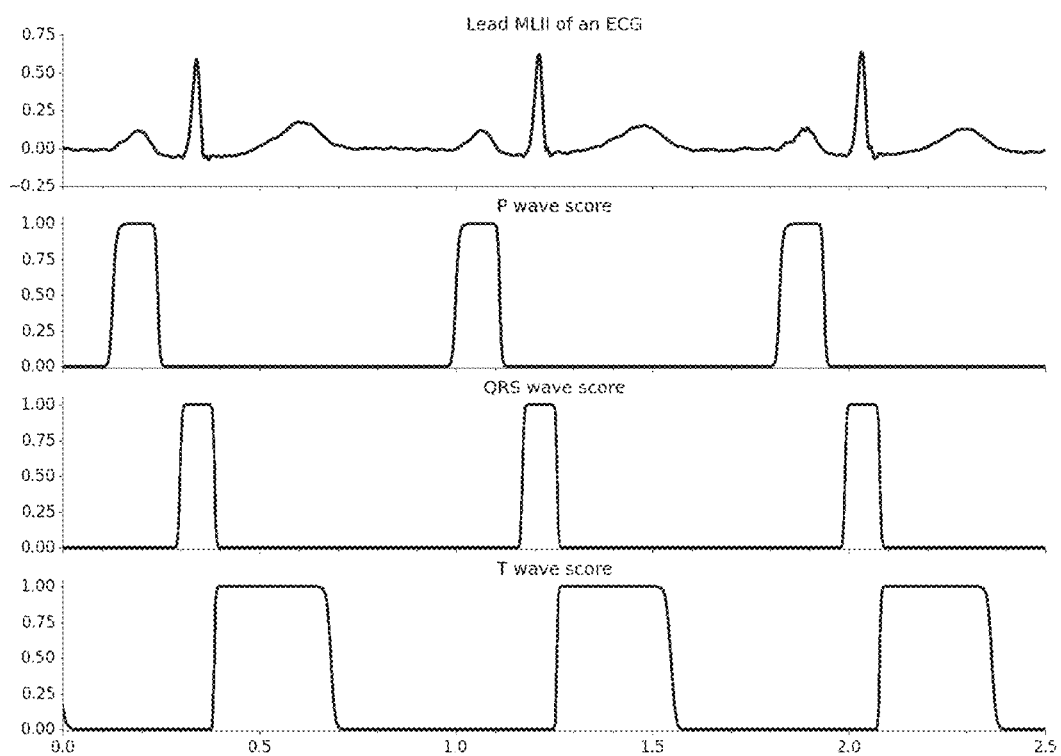
FIG. 4 is an example of the output of the delineation network on a normal ECG.
Figure 5:
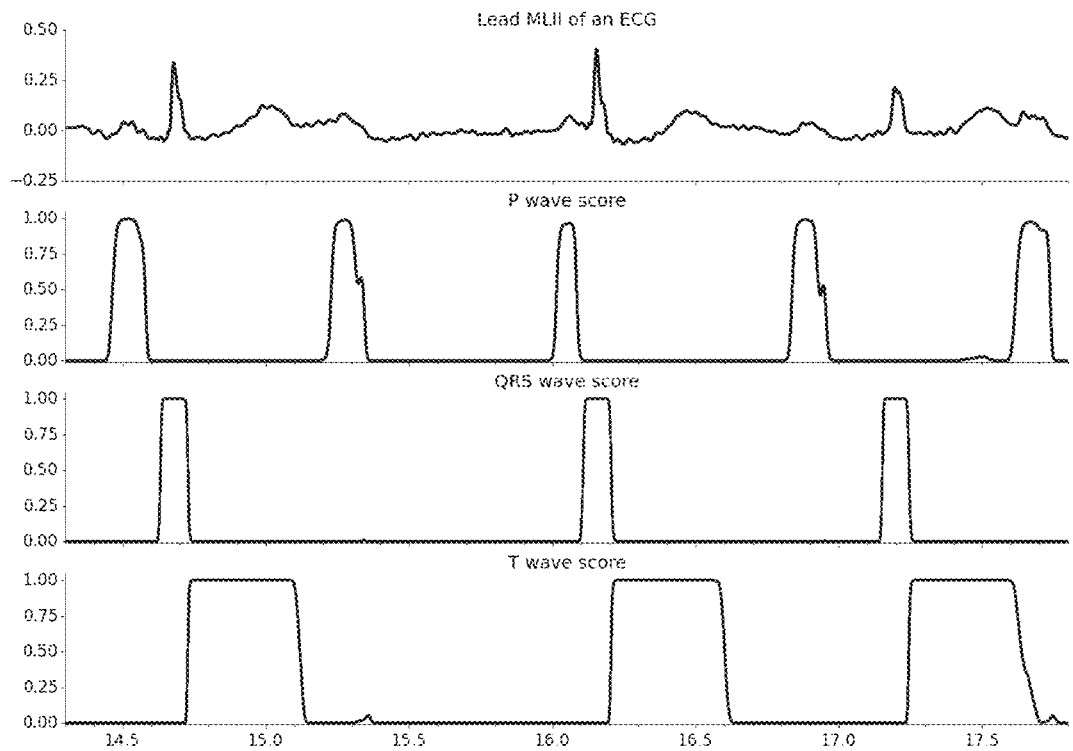
FIG. 5 is an example of the output of the delineation network on an ECG with hidden P waves (high degree atrioventricular block).
Figure 6:
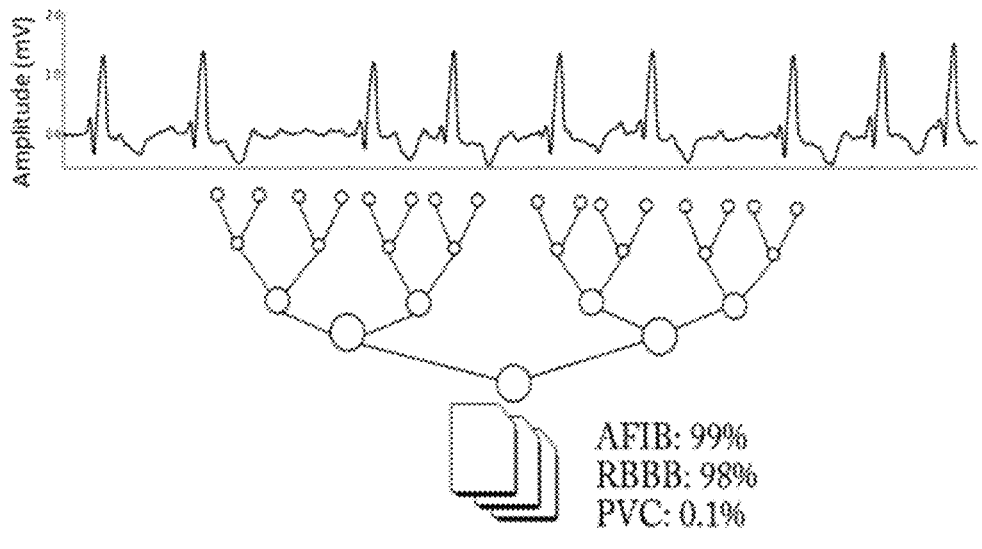
FIG. 6 models the way a standard multi-label convolutional network works.
Figure 7:
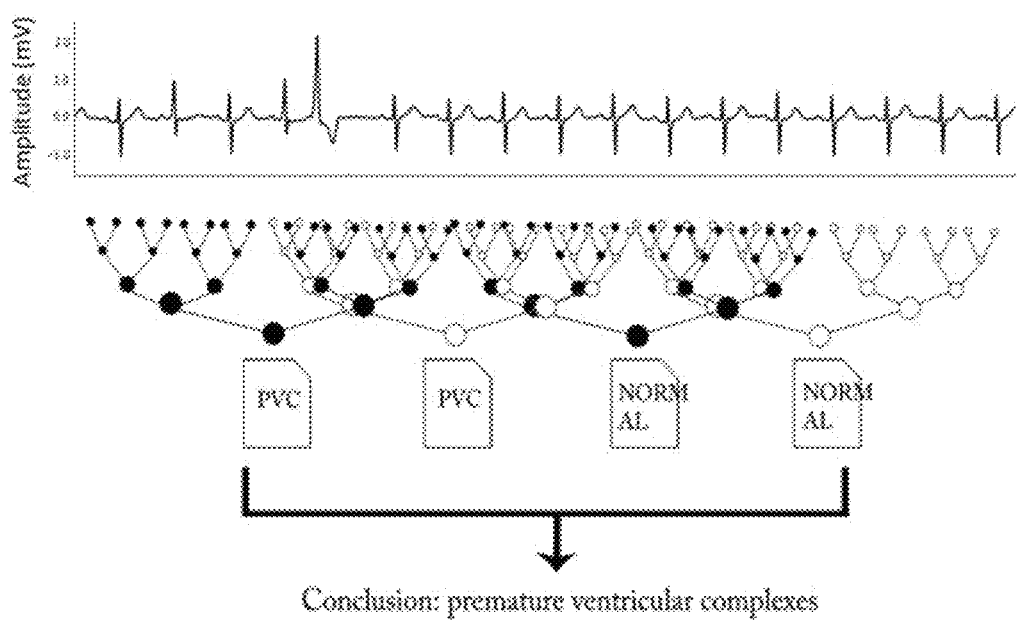
FIG. 7 models the way a multi-label recurrent convolutional network works.

The invention claimed is:

1. A computerized-method for classification of an electrocardiogram (ECG) signal obtained from a patient using a neural network, the computerized-method comprising:
   training the neural network with a dataset of pre-characterized ECG signals to generate a trained neural network;
   receiving the ECG signal sampled at a plurality of time points;
   analyzing the ECG signal at the plurality of time points using the trained neural network to compute anomaly scores based on the ECG signal to detect anomalies;
   assigning an anomaly label to the ECG signal for a detected anomaly based on the anomaly scores;
   defining an interval of time for the detected anomaly of the ECG signal according to time and based on the anomaly scores, the interval of time comprising length and location information in the ECG signal for the detected anomaly; and
   causing display of a representation of the ECG signal, the anomaly label, and the interval of time.

2. The computerized-method of claim 1, further comprising denoising and removing a baseline of the ECG signal.

3. The computerized-method of claim 1, further comprising determining a location of additional anomalies in the ECG signal.

4. The computerized-method of claim 1, further comprising assigning one or more additional anomaly labels to the ECG signal for at least one time point of the plurality of time points.

5. The computerized-method of claim 1, further comprising expressing the ECG signal at a selected frequency.

6. The computerized-method of claim 1, further comprising causing display of the anomaly scores.

7. The computerized-method of claim 1, further comprising assigning one or more additional anomaly labels to the ECG signal based on the anomaly scores for one or more additional detected anomalies,
   wherein causing display comprises causing display of the one or more additional anomaly labels.

8. The computerized-method of claim 1, wherein assigning the anomaly label to the ECG signal comprises assigning the anomaly label of atrial fibrillation to the ECG signal.

9. The computerized-method of claim 1, wherein:
   the neural network expresses the ECG signal as a matrix of size m×n with m being a number of leads fixed and at a predefined frequency and n being a number of samples.

10. The computerized-method of claim 1, further comprising expressing a plurality of detected anomalies as a vector of size q, with q being a number of anomalies to identify.

11. The computerized-method of claim 7, wherein at least one of the one or more additional anomaly labels correspond to a normal label.

12. The computerized-method of claim 7, further comprising defining one or more additional intervals of time for the one or more additional detected anomalies according to time and based on the anomaly scores,
   wherein causing display comprises causing display of the one or more additional intervals of time.

13. A system for classification of an electrocardiogram (ECG) signal obtained from a patient using a neural network, the system comprising at least one processor to:
   train the neural network with a dataset of pre-characterized ECG signals to generate a trained neural network;
   receive the ECG signal sampled at a plurality of time points;
   analyze the ECG signal at the plurality of time points using the trained neural network to compute anomaly scores based on the ECG signal to detect anomalies;
   assign an anomaly label to the ECG signal for a detected anomaly based on the anomaly scores;
   define an interval of time for the detected anomaly of the ECG signal according to time and based on the anomaly scores, the interval of time comprising length and location information in the ECG signal for the detected anomaly; and
   cause display of a representation of the ECG signal, the anomaly label, and the interval of time.

14. The system of claim 13, wherein the at least one processor is configured to denoise and remove a baseline of the ECG signal.

15. The system of claim 13, wherein the at least one processor is configured to determine a location of additional anomalies in the ECG signal.

16. The system of claim 13, wherein the at least one processor is further configured to assign one or more additional anomaly labels to the ECG signal for at least one time point of the plurality of time points.

17. The system of claim 13, wherein the at least one processor is configured to express the ECG signal at a selected frequency.

18. The system of claim 13, wherein the at least one processor is configured to cause display of the anomaly scores.

19. The system of claim 13, wherein the at least one processor is further configured to assign one or more additional anomaly labels to the ECG signal based on anomaly scores for one or more additional detected anomalies, and to cause display of the one or more additional anomaly labels with the representation of the ECG signal.

20. The system of claim 13, wherein the anomaly label comprises the anomaly label of atrial fibrillation.

21. The system of claim 13, wherein the at least one processor is configured to express the ECG signal as a matrix of size m×n with m fixed and at a predefined frequency.

22. The system of claim 13, wherein the at least one processor is configured to express one or more detected anomalies as a vector of size q, with q being a number of anomalies to identify.

23. The system of claim 19, wherein at least one of the additional anomaly labels correspond to a normal label.

24. A programmed routine comprising instructions that, when executed by at least one processor, cause the at least one processor to:

train the neural network with a dataset of pre-characterized ECG signals to generate a trained neural network;
receive the ECG signal sampled at a plurality of time points;
analyze the ECG signal at the plurality of time points using the trained neural network to compute an anomaly scores based on the ECG signal to detect anomalies;
assign an anomaly label to the ECG signal for a detected anomaly based on the anomaly scores;
define an interval of time for the detected anomaly of the ECG signal according to time and based on the anomaly scores, the interval of time comprising length and location information in the ECG signal for the detected anomaly; and
cause display of a representation of the ECG signal, the anomaly label, and the interval of time.

25. The programmed routine of claim 24, further comprising instructions that, when executed by the at least one processor, cause the at least one processor to denoise and remove a baseline of the ECG signal.

26. The programmed routine of claim 24, further comprising instructions that, when executed by the at least one processor, cause the at least one processor to determine a location of additional anomalies in the ECG signal.

27. The programmed routine of claim 24, further comprising instructions that, when executed by the at least one processor, cause the at least one processor to assign one or more additional anomaly labels to the ECG signal for at least one time point of the plurality of time points.

28. The programmed routine of claim 27, wherein at least one of the additional anomaly labels correspond to a normal label.

* * * * *